May 30, 1972 H. W. MILLER, JR Plant Pat. 3,198
NEW AND DISTINCT VARIETY OF APPLE TREE NAMED SPUREEROME
Filed Dec. 2, 1970
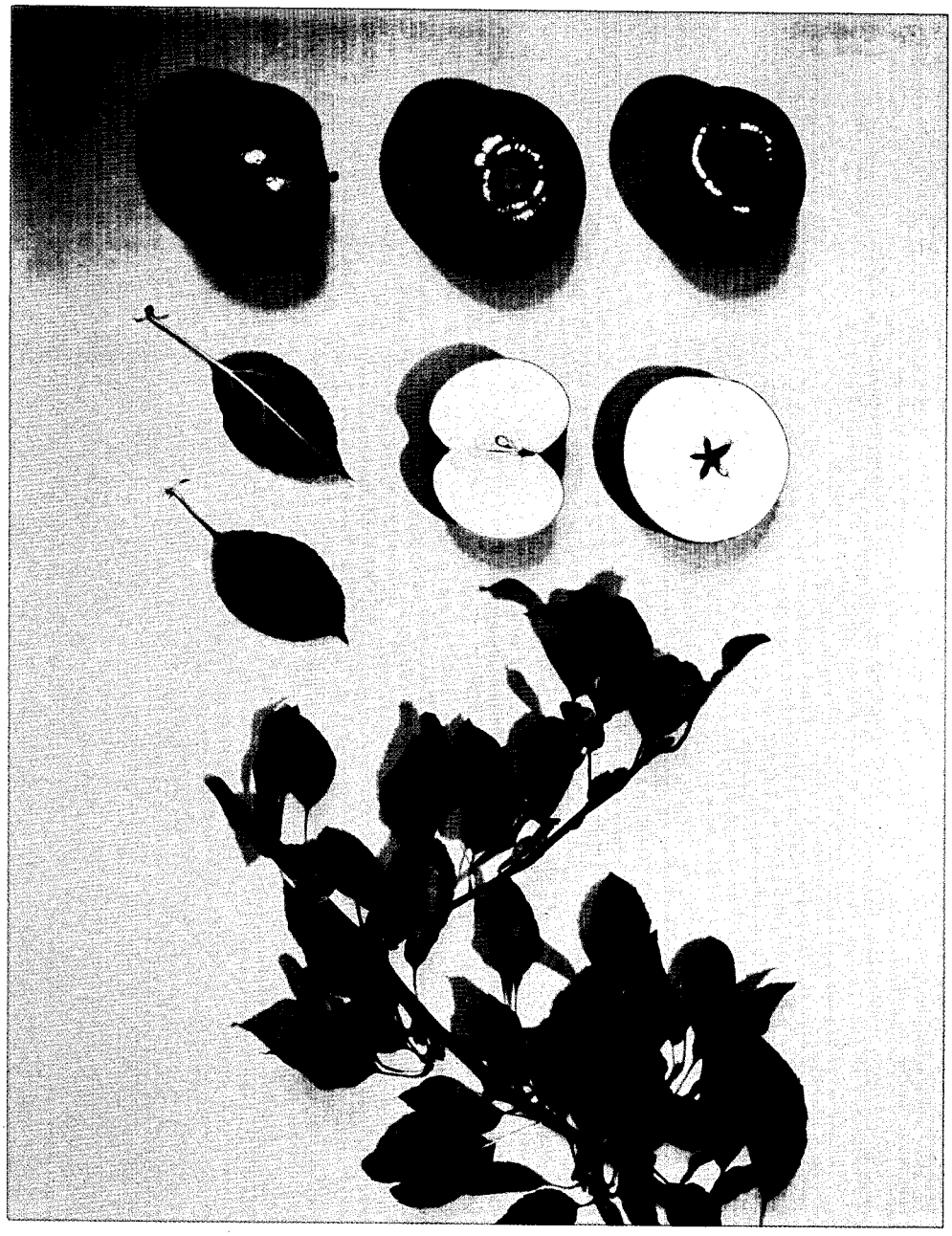
INVENTOR:
HENRY W. MILLER JR.
J R Nesbitt, ATTY.

United States Patent Office

Plant Pat. 3,198

Patented May 30, 1972

3,198
DISTINCT VARIETY OF APPLE TREE NAMED SPUREEROME

Henry W. Miller, Jr., Paw Paw, W. Va., assignor to Hill Top Orchards & Nurseries, Inc.

Filed Dec. 2, 1970, Ser. No. 94,635
Int. Cl. A01h 5/03
U.S. Cl. Plt.—34 1 Claim

The present invention relates to a new and distinct variety of apple tree discovered by Henry Miller as a whole tree sport in a block of regular "Red Rome" variety apple trees, said discovery having been made in the Hutchinson Placed Orchard of the Consolidated Orchard Company, Paw Paw, W. Va., of which company Mr. Miller is president. His attention was attracted to the new sport by the full, compact spur type growth habit of the tree, plus the full, bright color of the fruit throughout the tree. This apple tree variety has been named "Spuree Rome" by Hilltop Orchards and Nurseries, Inc., which owns the variety.

Further study and tests of the new sport, derived by grafting and also by budding, (performed by Consolidated Orchard Co. and others under their control and on their behalf; and by Hilltop Orchards and Nurseries, Inc. at Hartford, Mich.) convinced Mr. Miller that the spur type qualities (much more compact growing, with many more spurs and side shoots per length of limb than other known types of "Red Rome" and the bright color of the fruit, were fixed and established and were transmissible through succeeding propagations.

While "Spuree Rome" is similar in some respects to "Red Rome" in general and to "Gallia Beauty" in particular, it is definitely a new and distinct variety, distinguished therefrom and from all other apple varieties, and specifically distinguished therefrom and for "Gallia Beauty" in the following ways:

(1) The leaves have fewer, larger main veins, are more coarsely serrated, very pubescent on abaxial surface (underside of leaf), and have a more horizontal posture than "Gallia Beauty."

(2) The fruit is very highly colored, equal with the best known commercial strains of "Red Rome," the calyx is more open, wider, and less furrowed; the calyx lobes are smaller; the core is smaller; less heart-shaped, with alternate bundles, closer to the core.

(3) The one year old wood is darker color, more reddish; it exhibits more lenticels which are more conspicuous; and it is shorter jointed (shorter internodes) than "Gallia Beauty" and "Red Rome" strains in general. The buds located in the leaf petiole axis on one year old wood are larger, averaging about ¼" long and about ⅛" wide, and nearly ⅛" thick. "Gallia Beauty" buds on the same type wood are only about 1/16" long, ⅛" wide, and less than 1/16" thick, and are appressed.

(4) Seventy percent of the buds formed on one year shoot grow and produce either fruit spurs or vegetative shoots in the second year. Less than fifteen percent of "Gallia Beauty" buds grow in the second year, and those that do grow form slender lateral branches. This high percent of viable buds on "Spuree Rome," most of which form fruit spur, make the compact, "spur type" habit which is so unique, and which promotes fruiting throughout the entire tree.

The accompanying color photograph shows typical specimens of the foliage, branches, and fruit of this new variety of apple tree depicted as nearly true as it is reasonably possible to make the same in a color illustration of this character: with the foliage specimens depicting both the upper and lower surfaces of the leaves; the fruit specimens depicting both exterior and interior details of the fruit, one of which is shown in longitudinal cross-section and another in transverse section; side, top and bottom fruit views are depicted; and the branch specimen depicting the spur type character.

The following is a detail description of "Spuree Rome," with color terminology in accordance with Munsell's Nickerson Color Fan, except where general color terms of ordinary dictionary significance are obvious.

Locality where grown and observed: Paw Paw, W. Va., and Hartford, Mich. Dates of first and last pickings: October 15 and November 1, respectively.

Tree: Small size, medium vigor; moderately upright and droopy form; medium dense, much more dense than "Gallia Beauty." Vase form, tending toward a moderate Christmas tree form. Slow growing in the nursery, to medium rapid in the field. Hardy, very productive, and a regular bearer. Trunk: medium slender and smooth. Branches are medium slender to slender, smooth, with the many branches forming a dense appearing tree. Color: Greenish brown. Lenticels: (on one year bark) are numerous, scattered, large and raised.

Leaves: Average in length of 3" to 4" and width of 2" to 2¼"; medium size, width and length. In shape, oviate to oval, taper pointed, being of medium thickness and medium to dark green color; very smooth on axial surface and pubescent on abaxial. Margin, moderately serrate. Petiole about 1" in length, being medium along and medium slender.

Flowers: Similar to those of "Gallia Beauty," being medium late. Same in size and color as "Gallia Beauty."

Fruit: Eating hard, date, Oct. 12, 1970. Size: uniform; axial diameter 3" to 3¼"; transverse diameter, 2½". Form: uniform; symmetrical; regular; round to roundish conic; slightly oblong. Cavity: symmetrical; acuminate; even; obtuse; and gently furrowed to smooth. Moderately shallow; sometimes lipped; wide. Depth, ½" to ⅝"; breath, 1" to 1⅛". Markings: red to greenish red; not russeted. Basin: mostly symmetrical, sometimes abrupt; mostly flaring, base, narrow, usually somewhat furrowed; moderately angular; glabrous. Stem: clubbed, slender, glabrous. Length about 1" to 1⅛". Bracts are wanting. Calyx: mostly open to sometimes partially closed. Segments are persistent. Narrowly lanceolate; acuminate. Length about ¼". Separated at the base, erect, reflexed from the base. Outer and inner surfaces of calyx lobes are pubescent. Eve: medium and open. Skin: thick, tough, smooth, glossy, with a good wax coat. Dots are conspicuous to moderately noticeable, scattered, numerous, small, raised and ruptured in some years; they are circular, and whitish to fawn color, and distributed much heavier toward calyx end. Ground color is greenish to yellow; color markings are blushed, bright, 80% bright red blush washed over a slight greenish-yellow background. Bloom: wanting. Scarfskin is gray, and light, and distributed in streaks on shoulder of fruits, disappearing about one-half way down on the check. The general color effect is a very bright, almost solid red apple with some shaded areas of the fruit showing the greenish-yellow ground color, slightly masked with red. The shaded calyx end shows a 10 Yellow, 9/9 color notation (Munsell-Nickerson Color Fan), the light colored side partially shaded, 2.5 Red, 8/5, the heavy colored side 5 Red, 5/13 to Red 4/12. Flesh is juicy, color is white with slight greenish-yellow tinge. No red present in flesh. Texture is firm to hard; crisp; moderately fine. Flavor is mild, sub-acid, and delicate. Aroma is distant; Quality is good. Core, medium; bundle area (longitudinal section) medium, broadly cordate, unsymmetrical; actuate at base in bundle; alternate with cell. Halves of area are mostly unequal. Bundles are yellowing, inconspicuous, two whorls; alternate bundle is distant, reaches tube at stamens. Core lines are meeting, and in cross-section are indistinct; carpellary area is indistinct and small. Calyx tube is glabrous toward the base; apex is broadly cone shaped to funnel shaped. Length of funnel tube is short. Depth of tube approximately 1⅛". Entire depth, 1¼". Styles are fleshy at the base and present; united toward the base, and glabrous throughout. Stamens are in one distinct marginal whorl. Axillary cavity is wanting. Seed cells are abaxile and open. Cell walls are distant, thick, and tough. Length, approximately ¾"; breadth, approximately ⅜". Longitudinal section is narrowly oblong, mucronate. Surface is fissured and tufted along the fissures. Cross section is mostly broad. Seeds number from six to eight with no more than two per cell. They average in length from ¼" to 5/16", and in breadth approximately 3/16". Form is acuminate, color is reddish brown. Use is local, dessert, and culinary. Keeping quality is excellent, with ordinary storage of eight months or more. Resistance to insects approximately the same as "Gallia Beauty." Resistance to diseases: About the same as "Gallia Beauty."

I claim:

1. A new and distinct variety of apple tree substantially as herein shown and described, characterized by: a compact spur type vegetable growth habit which promotes fruiting throughout the entire tree; fruit that is highly colored, the core of which is small with alternate bundles close to the core; buds in the leaf petiole axis which are large; a high percent of variability of said buds in the second year, forming a very dense, heavily spurred tree.

No references cited.

ROBERT E. BAGWILL, Primary Examiner